United States Patent [19]
Rozov et al.

[11] Patent Number: 5,205,914
[45] Date of Patent: Apr. 27, 1993

[54] SYNTHESIS OF DESFLURANE

[75] Inventors: Leonid A. Rozov, Fair Lawn; Chialang Huang, Edison; Gerald G. Vernice, Nutley, all of N.J.

[73] Assignee: Anaquest, Inc., Liberty Corner, N.J.

[21] Appl. No.: 930,867

[22] Filed: Aug. 14, 1992

[51] Int. Cl.$^5$ .............................................. C07C 17/00
[52] U.S. Cl. ............................ 204/157.94; 204/157.6; 204/157.15; 568/683
[58] Field of Search .................... 204/157.94; 568/683

[56] References Cited

U.S. PATENT DOCUMENTS 3,242,218 3/1966 Miller .................................. 568/683
5,026,924 6/1991 Cicco .................................. 568/683

Primary Examiner—John Niebling
Assistant Examiner—C. Delacroix-Muirheid
Attorney, Agent, or Firm—R. Hain Swope; Larry R. Cassett

[57] ABSTRACT

An improved preparation of desflurane, 1,2,2,2-tetrafluoroethyl difluoromethyl ether utilizing hexafluoropropene epoxide as a starting material. Hexafluoropropene epoxide is advantageous in that it is relatively inexpensive and is environmentally acceptable.

10 Claims, No Drawings

SYNTHESIS OF DESFLURANE

This invention pertains to a new synthetic route for the inhalation anesthetic, desflurane.

BACKGROUND OF THE INVENTION

Desflurane, 1,2,2,2-tetrafluoroethyl difluoromethyl ether ($CF_3CHFOCHF_2$), is an inhalation anesthetic presently awaiting regulatory approval for marketing in the United States. The use of desflurane as an inhalation anesthetic is claimed in Terrell, U.S. Pat. No. 4,762,856, issued Aug. 9, 1988. Desflurane was originally disclosed in Example XXI of Russell et al U.S. Pat. No. 3,897,502, issued Jul. 29, 1975, which is directed to a method of fluorinating ethers to make compounds generally useful as solvents, degreasing agents and the like.

Desflurane has commercial potential as an inhalation anesthetic, particularly for outpatient procedures, because of its rapid rate of recovery and extremely low metabolism. As a result, there has been considerable effort devoted to finding an optimal synthesis therefor.

One method of preparing desflurane is by first converting fluoral methyl hemiacetal to 1,2,2,2-tetrafluoroethyl methyl ether ($CF_3CHFOCH_3$) which is then chlorinated to produce a compound having the formula $CF_3CHFOCHCl_2$. The resulting compound is fluorinated with HF in the presence of antimony pentachloride. See, for example, German Offen. 2,361,058 (1975). This is a complex, expensive process which is not suited to industrial scale.

More recently, a number of processes for preparing desflurane have been patented. Halpern et al, U.S. Pat. No. 4,855,511, issued Aug. 8, 1989. discloses preparing desflurane by the reaction of a compound having the formula $CHCl_2OCHClCOCl$ with sulfur tetrafluoride at elevated temperatures. Halpern et al, U.S. Pat. No. 4,874,901, issued Oct. 17, 1989, discloses a method of fluorinating a chlorine on the carbon adjacent the ether oxygen in chloro-fluoro ethers by reaction with sodium or potassium fluoride at elevated temperature and pressure in the absence of solvent. By this method, isoflurane ($CF_3CHClOCHF_2$) is converted to desflurane.

In Robin et al, U.S. Pat. No. 4,972,040, issued Nov. 20, 1990, fluoral methyl hemiacetal, $CF_3CH(OH)OCH_3$, is reacted with p-toluene sulfonyl chloride to form the corresponding tosylate compound. The tosylate group is then removed by reaction with a fluorinating agent to form $CF_3CHFOCH_3$. This compound is converted to desflurane by chlorinating the methyl group, preferably with chlorine gas, followed by reaction with a fluorinating agent.

Robin et al. U.S. Pat. No. 5,015,781, issued May 14, 1991, disclosed a process for forming desflurane by the direct fluorination of isoflurane ($CF_3CHClOCHF_2$) by bromine trifluoride. Cicco, U.S. Pat. No. 5,026,924, issued Jun. 25, 1991, discloses a low temperature preparation of desflurane comprising reacting isoflurane with hydrogen fluoride in the presence of a catalyst comprising antimony pentachloride, alone or in combination with antimony trichloride.

These methods, although adequate, can be improved upon with regard to a number of particulars. The synthesis utilizing sulfur tetrafluoride, for example is disadvantageous because it is not commercially available and is considered very toxic. The processes wherein desflurane is formed from isoflurane are disadvantageous in that the preparation of isoflurane according to the following reaction $$CF_3CH_2OH + CF_2ClH + NaOH \rightarrow CF_3CH_2OCF_2H$$

$$CF_3CH_2OCF_2H + \tfrac{1}{2}Cl_2 \rightarrow CF_3CHClOCF_3H + HCl$$

utilizes trifluoroethanol which is expensive and chlorodifluoromethane which is not considered favorable to the environment.

Accordingly, there exists a need for a synthesis of desflurane which is efficient, utilizes relatively inexpensive starting materials, and is environmentally acceptable. Such a process is provided in accordance with the present invention.

BRIEF SUMMARY OF THE INVENTION

Desflurane is prepared by reacting hexafluoropropene epoxide with methanol to form methyl 2-methoxytetrafluoropropionate which is hydrolyzed to the corresponding acid. The acid is decarboxylated to form 1,2,2,2-tetrafluoroethyl methyl ether which is then chlorinated to form 1,2,2,2-tetrafluoroethyl dichloromethyl ether. Fluorine-chlorine exchange of the ether by conventional fluorination produces desflurane.

DETAILED DESCRIPTION OF THE PREFERRED EMBODIMENTS

In accordance with the present invention, desflurane, i.e. 1,2,2,2-tetrafluoroethyl difluoromethyl ether ($CF_3CHFOCHF_2$), is prepared in five steps utilizing as a starting material hexafluoropropene epoxide

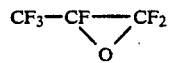

which is a known material and commercially available. Hexafluoropropene epoxide is advantageous as a starting material in that it is stable, readily available, comparatively inexpensive, and environmentally safe.

In the first step of the subject synthesis, hexafluoropropene epoxide is reacted with methanol to form methyl 2-methoxytetrafluoropropionate according to the reaction

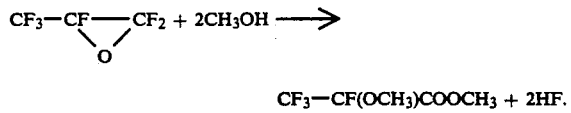

$$CF_3-CF(OCH_3)COOCH_3 + 2HF.$$

This reaction which is described by Sianesi et al, *J. Org. Chem.*, A2312 (1966). Vol. 31. may be carried out under pressure, or at ambient pressure simply by passing gaseous hexafluoropropene epoxide through methanol. The reaction proceeds in high yield, and the product ester can be further processed in the system without purification.

Methyl 2-methoxytetrafluoropropionate is hydrolyzed to form the corresponding acid by heating under reflux with aqueous base, preferably an inorganic base, such as aqueous potassium hydroxide. The acid is then decarboxylated by heating in the presence of a glycol, such as triethylene glycol or diethylene glycol, and aqueous base to give 1,2,2,2-tetrafluoroethyl methyl ether according to the reaction

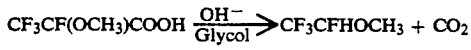

The ether is then chlorinated by conventional means such as by chlorine gas in the presence of ultraviolet or incandescent light. It has been found that conventional photochlorination carried out until the starting ether is no longer detectable in the reaction mixture is not satisfactory. This is because there is produced a mixture of predominately monochloro and dichloro ethers, i.e. $CF_3CFHOCH_2Cl$ and $CF_3CFHOCHCl_2$, and some trichloro ether, $CF_3CFHOCCl_3$ which is not separable by fractional distillation without a significant loss. There is also the necessity of recycling the monochloro ether to the chlorination reaction.

It is instead preferred in accordance with the present invention that the chlorination be carried out until the monochloro ether is no longer detectable in the reaction mixture. At this point, the reaction mixture will be comprised of the dichloroether and the trichloroether in a ratio of approximately 3:2. The crude reaction mixture can be treated with UV irradiation in the presence of a lower alkanol, preferably isopropanol, to effectively reduce the trichloro ether to the dichloroether.

Finally, the dichloroether, $CF_3CFHOCHC_2$, is fluorinated to replace both chloro substituents with fluoro substituents thereby forming desflurane $CF_3CFHOCHF_2$. This reaction may be carried out utilizing any of the conventional reagents recognized by those skilled in the art to effect a fluoro/chloro exchange in such halogenated ethers. Preferred reagents include hydrogen fluoride in the presence of antimony pentachloride as a catalyst and bromine trifluoride. The desflurane thus produced is isolated, purified, and packaged.

In accordance with the present invention, two or more of the foregoing steps may be carried out sequentially without isolation or purification of the intermediate product. For example, 2-methoxytetrafluoropropionic acid may be formed from hexafluoropropene epoxide by bubbling the latter through a mixture of methanol and an aqueous solution of a suitable base, preferably sodium or potassium hydroxide, for 6 to 15 hours, diluting the reaction mixture with water and neutralizing with acid. The mixture is thereafter evaporated to remove water and methanol, the residue taken up in concentrated phosphoric acid, and the resulting solution distilled to give a fraction which separates into two layers, with the desired acid as the organic layer. This reaction may suitably be carried out under pressure and in a continuous manner.

In order to run the reaction under pressure, a mixture of the base and methanol is cooled to a temperature of from about $-75°$ to $-100°$ C., and the requisite amount of hexafluoropropene epoxide condensed therein. Cooling is discontinued, and the temperature allowed to rise to about 50° C. The reaction requires from about 1-2 hours at an autogeneously developed pressure of 175-200 psig. The mixture is thereafter neutralized, evaporated, and the solid taken up with acid, preferably phosphoric acid, and fractionally distilled to obtain the product acid.

In a preferred embodiment, 1,2,2,2-tetrafluoroethyl methyl ether can be prepared from methyl 2-methoxytetrafluoropropionate without isolation of the intermediate acid, either with or without added water. 1,2,2,2-tetrafluoroethyl methyl ether can also be formed directly from hexafluoropropene epoxide in a simplified procedure conducted in a single reaction vessel.

In the latter procedure, hexafluoropropene epoxide is bubbled through a mixture of water, methanol and sodium methoxide at a temperature of from about 50° to 75° C. The mixture is stirred overnight, neutralized with a suitable acid, and the low boiling components evaporated. The residue is taken up in water, combined with diethylene glycol and gradually heated to 300° C. to cause in situ decarboxylation of the 2-methoxytetrafluoropropionic acid. The resulting ether is collected over dry ice.

The embodiments of the present invention wherein the reactions beginning with hexafluoropropene epoxide and forming methyl 1,2,2,2-tetrafluoroethyl ether are preferably carried out sequentially in a single vessel without isolation and purification of intermediate products. In addition, it is preferred that the step of forming methyl 1,2,2,2-tetrafluoroethyl ether from methyl-2-methoxytetrafluoropropionate be carried out under decarboxylation conditions such as, for example, heating in the presence of glycol and a strong base.

Further characteristics and descriptions of desflurane and anesthetic compositions containing it are found in Terrell, U.S. Pat. No. 4,762,856.

The following examples more fully illustrate the preferred embodiments of the synthesis according to this invention. Such examples are intended for illustration only and not to limit the scope of this invention. All temperatures are in degree Celsius unless otherwise noted.

EXAMPLE 1

Gaseous hexafluoropropene epoxide (388.0 g) was bubbled at room temperature through 1000 ml of methanol contained in a 2L flask equipped with a magnetic stirring bar, a gas inlet tube, a dry ice condenser and a thermometer. The addition consumed 15 hours. After the completion of the mild exothermic reaction, water (1000 ml) was added to the reaction mixture and the resulting organic layer was separated, washed twice with water and dried over calcium chloride. Distillation gave methyl 2-methoxytetrafluoropropionate, $CF_3CF(OCH_3)COOCH_3$ (385.0 g, 87%) b.p. 42° (20 mm Hg).

EXAMPLE 2

A mixture of methyl 2-methoxytetrafluoropropionate formed in Example 1 (41.9 g), water (500 ml) and potassium hydroxide (56 g) was refluxed for 3 hours. The reaction mixture was acidified with 100 ml of equal parts hydrochloric acid and water and extracted with three 200 ml portions of ether. The combined ether extracts were dried over sodium sulfate. After evaporation of the ether, fractional distillation gave 2-methoxytetrafluoropropionic acid (31.0 g. 80%), b.p. 67°-68° (12 mm Hg).

EXAMPLE 3

A mixture of 2-methoxytetrafluoropropionic acid formed in Example 2 (8.4 g, 0.048 mol), 85% potassium hydroxide (3.7 g, 0.056 mol). water (15.4 g, 0.86 mol) and diethyleneglycol (11.5 g , 0.114 mol) was heated in a distillation apparatus connected to two dry ice traps and a bubbler. After the distillation of water was completed, the temperature of the reaction mixture was slowly increased up to 250°. The evolution of gases started at about 180°. The product (approx. 2 ml), which collected in the traps, was kept at room temperature with a dry ice condenser until the evolution of low boiling material stopped. It was washed with cold water and dried over calcium chloride. Distillation gave 1.5 g (24%) of 96% 1,2,2,2-tetrafluoroethyl methyl ether, b.p. 36°–38°.

EXAMPLE 4

A mixture of methyl-2-methoxy-tetrafluoropropionate formed in Example 1 (100.0 g. 0.53 mol). 85% potassium hydroxide (39.3 g. 0.6 mol) and water (95.0 g. 5.3 mol) was heated under reflux for two hours. The mixture was cooled, triethylene glycol (156.0 g, 1.04 mol) was added and the reaction continued in the manner of Example 3. Distillation gave 34.8 g (50%) of 1,2,2,2-tetrafluoroethyl methyl ether, bp 39°–40°.

The reaction was repeated without water in the following manner. A mixture of methyl 2-methoxytetrafluoropropionate (47.5 g. 0.25 mol), 85% potassium hydroxide pellets (16.1 g, 0.25 mol) and triethylene glycol (112.6 g, 0.75 mol) was slowly heated in a distillation apparatus similar to that utilized in Example 3. At 100°, the mixture became homogeneous and methanol began to distill off. The evolution of carbon dioxide began at 200°. The temperature of the mixture reached 250° and was maintained for two hours. Distillation yielded 16.2 g (49% yield) of product.

EXAMPLE 5

A 100 ml jacketed glass cylindrical reactor equipped with a magnetic stirring bar, thermometer, gas dispersion tube, and dry ice condenser which was connected to an empty flask, followed by a water scrubber, was charged with 124.7 g (0.95 mol) of 1,2,2,2-tetrafluoroethyl methyl ether formed in Example 3. Chlorine gas was slowly bubbled into it while the reactor was irradiated with a 250 watt incandescent light at +10° to +15°. The chlorination reaction was terminated when the reaction mixture consisted of 58.5% of the dichloro product ($CF_3CFHOCHCl_2$) and 38.3% of the trichloro product ($CF_3CFHOCCl_3$). It was washed with water. sodium bicarbonate solution, and again with water, and dried over calcium chloride. The crude products (188.8 g) were subjected to fractional distillation to obtain the following analytical samples:

1,2,2,2-tetrafluoroethyldichloromethyl ether ($CF_3CFHOCHCl_2$) b.p. 81°–84°;
1,2,2,2-tetrafluoroethyltrichloromethyl ether ($CF_3CFHOCCl_3$), b.p. 96°–97°.

Elemental analysis for $CF_3CFHOCCl_3$: Calc'd: C 15.31; H 0.43; Cl 45.18%; Found: C 15.45; H 0.38; Cl 44.80%.

EXAMPLE 6

A mixture of 7.0 g, (0.03 mol) of 1,2,2,2-tetrafluoroethyltrichloromethyl ether formed in Example 5 and 20.0 g of 2-propanol was placed in a 50 ml Pyrex 3-neck flask equipped with a magnetic stirring bar, a gas inlet tube, and a dry ice condenser which was connected to a cold trap (−78°). The mixture was irradiated with a 450 watt medium pressure mercury UV-immersion lamp (Canrad-Hanovia) at 10 cm distance at room temperature for three hours during which a low flow of nitrogen was passed into the reaction vessel. The reaction mixture was washed with $H_2O$ and aqueous sodium bicarbonate and dried over calcium chloride. Distillation gave 3.9 g of fraction b.p. 81°–83°, containing 91% of 1,2,2,2-tetrafluoroethyldichloromethyl ether $CF_3CFHOCHCl_2$ (GC, NMR). Yield (GC) 59%.

A mixture of the chlorinated ethers from fractional distillation in Example 5 (86.0 g) having the following composition (based on GC area %): $CF_3CFHOCHCl_2$—70%, $CF_3CFHOCCl_3$—30%, and 200 g of 2-propanol was subjected to the same treatment as above. Distillation afforded a fraction with b.p. 81°–84°, (60.0 g, 89% pure) identical (GC, NMR) to 1,2,2,2-tetrafluoroethyldichloromethyl ether, reported above.

EXAMPLE 7

A 25 ml 3-neck flask equipped with a magnetic stirrer, a poly(tetrafluoroethylene) coated thermometer, a graduated addition funnel and a dry ice condenser connected to an ice water trap, followed by a dry ice trap was charged under nitrogen with 10.0 g (89.1%, 44.4 mmol) of 1,2,2,2-tetrafluoroethyl dichloromethyl ether and 0.2 ml of bromine, which acts as a reaction promoter. The mixture was cooled to −15°, and bromine trifluoride (3.4 ml, 69.5 mmol) was added, dropwise, over a period of 100 minutes. The reaction temperature was maintained between −15° and −7°. After addition was completed, the reaction mixture was stirred at −5° for one hour, then warmed to 0° with a water bath. At this point, dry ice in the condenser was removed to allow the low boiling products to distill over. The reaction pot was gradually heated to 47° to push over the remaining products. The pot residue was cooled to −5°, and both traps were replaced with new dry ice traps. An ice cold 10% sodium hydroxide solution was cautiously added to destroy bromine and unreacted bromine trifluoride. The material in all four traps was washed with 10% sodium hydroxide solution. The organic liquids were combined and washed with 10% sodium hydroxide solution again followed by water (2×20 ml). Water was removed from the organic layer in dry ice. This treatment afforded 3.7 g of 1,2,2,2-tetrafluoroethyl difluoromethyl ether, 92.8% pure by GC analysis.

EXAMPLE 8

A polytetrafluoroethylene reaction flask was charged with 5.7 g (285.0 mmol) of anhydrous hydrogen fluoride and 0.3 g (1.0 mmol) of antimony pentachloride at −5° under nitrogen. 1,2,2,2-tetrafluoroethyl dichloromethyl ether 4.9 g (77.3% pure, 18.8 mmol), was added to the mixture at the same temperature over a period of 20 minutes. The reaction mixture was warmed up to room temperature over 1½ hours, then heated using a water bath to 37° to drive the reaction to completion. The reaction mixture was cooled again in ice water and was neutralized with 13% aqueous sodium hydroxide solution. Liquids collected in the traps were also neutralized. The organic liquids were combined and washed with water. An organic liquid was dried by freezing in dry ice. This afforded 0.3 g of a clear liquid which contained 69.5% of 1,2,2,2-tetrafluoroethyl difluoromethyl ether (GC).

EXAMPLE 9

This example illustrates the direct preparation of 2-methoxytetrafluoropropionic acid from hexafluoropropene epoxide. A mixture of 195.8 g of 50% aqueous sodium hydroxide solution and 325 ml of methanol was placed in 1L, 3-neck flask equipped with a stirring bar, a thermometer, a dry ice condenser, and a gas inlet tube. Hexafluoropropene epoxide (31.5 g, 0.19 mol) was bubbled through this mixture at room temperature over a period of 8 hours. The resulting white slurry was stirred overnight. Water (100.0 g) was added, and the reaction mixture was gradually neutralized with concentrated hydrochloric acid (200 g). Rotary evaporation of water and methanol afforded 166.5 g of a white solid which was ground to powder. The powder was mixed with 100.5 g of 99% phosphoric acid and distilled to give a fraction b.p. 35°–43° (7 mm Hg) which consisted of two layers. The organic layer (26.9 g) was redistilled to afford 23.3 g (69.4%) of the 2-methoxytetrafluoropropionic acid ($^1$H NMR), b.p. 55°–60° (7 mm Hg).

EXAMPLE 10

The synthesis of Example 9 was carried out under pressure as follows. A 100 ml stainless steel stirred reactor chilled to 0° was charged with 32.8 g of aqueous sodium hydroxide solution and 50.1 g of methanol. The reactor was cooled to −78° and 23.7 g (0.143 mol) of hexafluoropropene epoxide was condensed therein. The cooling bath was removed, and stirring was started. The reaction temperature rose to 50°, and the pressure to 185 psig. The reaction was completed in an hour, but stirring was continued for another hour. The reaction mixture was neutralized by 3 g of 50% aqueous sodium hydroxide solution. The low boilers were removed by evaporation, and the resulting white solid (40.6 g) was combined with 40.7 g of 99% phosphoric acid and distilled to afford 17.1 g (67.9%) of 2-methoxytetrafluoropropionic acid ($^1$H NMR) b.p. 55°–60° (7 mm Hg).

EXAMPLE 11

This example illustrates the preparation of 1,2,2,2-tetrafluoroethyl methyl ether from hexafluoropropene epoxide in a single reaction vessel without isolation or purification of intermediates. Hexafluoropropene epoxide (12.4 g, 0.075 mol) was bubbled at room temperature over a period of six hours into a mixture at 100.0 g of 25% sodium methoxide in methanol and 60.0 g of water. The reaction mixture was stirred overnight and then neutralized with 18% hydrochloric acid solution (97.0 g). After the evaporation of the low boilers, the remaining solid (32.3 g) was dissolved in water (150 ml), diethylene glycol (49.8 g) was added and the resulting solution was gradually heated to 300° to facilitate the decarboxylation of 2-methoxytetrafluoropropionic acid formed in situ. The product, collected in a dry ice trap (0.1 g) was 98% pure (GC, NMR).

We claim:

1. A process for the preparation of 1,2.2,2-tetrafluoroethyl difluoromethyl ether comprising:
   (a) reacting hexafluoropropene epoxide with methanol to yield methyl 2-methoxytetrafluoropropionate;
   (b) hydrolyzing the product of step (a) to form 2-methoxytetrafluoropropionic acid;
   (c) decarboxylating said acid to form 1,2,2,2-tetrafluoroethyl methyl ether;
   (d) chlorinating said ether to form $CF_3CFHOCHCl_2$; and
   (e) reacting the product of step (d) with a fluorinating agent to form 1,2,2,2-tetrafluoroethyl difluoromethyl ether.

2. A process in accordance with claim 1, wherein the product of step (a) is hydrolyzed to form 2-methoxytetrafluoropropionic acid by heating in an aqueous base.

3. A process in accordance with claim 1, wherein the acid formed in step (b) is decarboxylated by heating in the presence of a glycol and an aqueous base.

4. A process in accordance with claim 1, wherein steps (b) and (c) are carried out in the same reaction vessel without isolation of purification of the intermediate product.

5. A process in accordance with claim 1, wherein steps (a) through (c) are carried out in the same reaction vessel without isolation or purification of intermediate products.

6. A process in accordance with claim 1, wherein said chlorination in step (d) is carried out by reacting the ether formed in step (c) with chlorine gas in the presence of ultraviolet light or incandescent light.

7. A process in accordance with claim 6, wherein said chlorination forms a mixture of $CF_3CFHOCH_2Cl$ $CF_3CFHOCHCl_2$ and $CF_3CFHOCCl_3$, and said chlorination is carried out until neither the ether formed in step (c) nor $CF_3CFHOCH_2Cl$ remains in the reaction mixture, thereby forming a mixture of $CF_3CFHOCHCl_2$ and $CF_3CFHOCCl_3$.

8. A process in accordance with claim 7, wherein said process additionally includes the step of reducing $CF_3CFHOCCl_3$ to form $CF_3CFHOCHCl_2$.

9. A process in accordance with claim 8, wherein said reduction is carried out by irradiating the reaction with ultraviolet light in the presence of a lower alkanol.

10. A process in accordance with claim 1, wherein said fluorinating agent is bromine trifluoride or hydrogen fluoride in the presence of antimony pentachloride.

* * * * *